United States Patent [19]

Unruh et al.

[11] Patent Number: 5,081,285
[45] Date of Patent: Jan. 14, 1992

[54] PRODUCTION OF ETHYL 3-ETHOXYPROPANOATE BY ACID CATALYZED ADDITION OF ETHANOL TO ETHYL ACRYLATE

[75] Inventors: Jerry D. Unruh, Corpus Christi, Tex.; Jerry A. Broussard, Summit, N.J.

[73] Assignee: Hoechst Celanese Corporation, Somerville, N.J.

[21] Appl. No.: 659,790

[22] Filed: Feb. 21, 1991

Related U.S. Application Data

[63] Continuation-in-part of Ser. No. 504,780, Apr. 4, 1990, abandoned.

[51] Int. Cl.$^5$ .............................................. C07C 69/66
[52] U.S. Cl. .................................................. 560/187
[58] Field of Search ......................................... 560/187

[56] References Cited

U.S. PATENT DOCUMENTS

| | | | |
|---|---|---|---|
| 2,386,363 | 10/1945 | Souther | 560/187 |
| 2,436,286 | 2/1948 | Brooks | 560/187 |
| 3,134,807 | 5/1964 | Enk | 560/187 |
| 4,785,133 | 11/1988 | Raynolds et al. | 560/187 |
| 4,827,021 | 5/1989 | Jones et al. | 560/187 |
| 4,927,954 | 5/1990 | Knopf et al. | 560/187 |
| 4,948,915 | 8/1990 | Keen | 560/187 |
| 5,011,977 | 4/1991 | Jones et al. | 560/187 |

FOREIGN PATENT DOCUMENTS 3310905  9/1984  Fed. Rep. of Germany ...... 548/239

OTHER PUBLICATIONS

Lapkin et al., Chem. Abstr., vol. 69, entry 2479m (1968).
Fuelbier et al., Chem. Abstr., vol. 102, entry 61808v (1985), Abstracting DD 212733.

Primary Examiner—Donald G. Daus
Attorney, Agent, or Firm—Donald R. Cassady

[57] ABSTRACT

This invention pertains to the addition of an alkyl alcohol to an alkyl acrylate to form alkyl 3-alkoxy propanoate catalyzed by a strong acid catalyst. The process has sepcific application in the addition of ethanol to ethyl acrylate to form ethyl 3-ethoxy propanoate.

5 Claims, No Drawings

PRODUCTION OF ETHYL 3-ETHOXYPROPANOATE BY ACID CATALYZED ADDITION OF ETHANOL TO ETHYL ACRYLATE

RELATIONSHIP TO PRIOR APPLICATIONS

This application is a continuation-in-part of application Ser. No. 07/504,780, filed Apr. 4, 1990, now abandoned.

BACKGROUND OF THE INVENTION

The present invention is directed to a novel process for producing ethyl 3-ethoxypropanoate (EEP).

Ethoxyethyl acetate is a known industrial solvent having a wide variety of uses such as in coatings, paints, inks, etc. It is suspected, however, that ethoxyethyl acetate is a possible carcinogen. A potential non-carcinogenic substitute for ethoxyethyl acetate is believed to be ethyl 3-ethoxypropanoate (EEP).

Souther, in U.S. Pat. No. 2,386,363, describes the manufacture of EEP by heating a mixture of β-ethoxypropionitrile and absolute ethanol with sulfuric acid and water in the following molar quantities 1:2:1:1 at a temperature of 99°–105° C. for from 12–24 hours.

Jones et al, in U.S. Pat. No. 4,827,021, describes the manufacture of alkyl 3-alkoxypropionates by the reaction of dialkoxy methane with a diketene. The catalyst for the reaction was methane disulfonic acid, methane trisulfonic acid, or mixtures thereof.

Brooks, U.S. Pat. No. 2,436,286, describes the reaction of dialkoxy methane with ketene in the presence of benzene sulfonic acid to form EEP and analogs thereof.

It is also known to produce EEP by the addition of ethanol to ethyl acrylate in the presence of a strong basic catalyst as is consistent with known methods, in general, of adding alcohols across the double bond of acrylate esters using strong bases as catalysts. Strong base catalysts which are useful in the formation of EEP include alkali metal alkoxides such as sodium ethoxide, potassium ethoxide and lithium ethoxide. While these catalysts have produced EEP in high efficiencies, the catalysts are extremely sensitive to moisture and readily deactivate in the presence of water. Accordingly, both the ethanol and ethyl acrylate reactants must be extremely dry. To provide the ethanol and ethyl acrylate reactants devoid of water is both a difficult and expensive process, thus, discouraging the manufacture and, thus, use of EEP. Examples of this reaction are to be found in Keen, U.S. Pat. No. 4,948,915, and the references cited therein.

Accordingly, it would be worthwhile to produce EEP in a manner which does not require the extensive preparation of the reactants to remove water and which can be done economically to meet the growing market for this non-carcinogenic solvent.

SUMMARY OF THE INVENTION

It has now been discovered that ethyl 3-ethoxypropanoate (EEP) can be produced by the acid catalyzed addition of ethanol to ethyl acrylate at greater than 90% efficiency for both ethanol and ethyl acrylate.

DETAILED DESCRIPTION OF THE INVENTION

The formation of EEP by the addition of ethanol to ethyl acrylate can be depicted as follows:

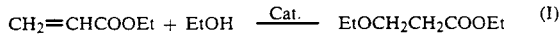

$$CH_2=CHCOOEt + EtOH \xrightarrow{Cat.} EtOCH_2CH_2COOEt \quad (I)$$

Previous to this invention, the above reaction was catalyzed by strong basic catalysts such as alkali metal alkoxides. It has now been found that the addition of ethanol to ethyl acrylate can be catalyzed by strong acid catalysts. Among the catalysts which are useful include the strong mineral acids, such as sulfuric acid, hydrochloric acid, and phosphoric acid; strong organic acids, such as the sulfonic acids, including methane sulfonic acid, benzene sulfonic acid, and toluene sulfonic acids; and sulfonic acid-type ion exchange resins.

The reaction can occur at temperatures as low as 75° C. and can range from about 75°–200° C., preferably between 120°–150° C. and, more preferably from about 120°–130° C. Inasmuch as ethanol boils at 78° C., the reaction needs to be run at increased pressure such as about 30–100 psig, preferably from about 40–50 psig. at the preferred temperature range. Reaction times range from about 1 to 8 hours, preferably 2 to 6 hours to obtain acceptable yields.

The major by-product of the reaction is diethyl ether which results from the condensation of ethanol. Diethyl ether by-product formation is temperature dependent and appears to increase with increasing temperature. Another by-product results from the oligomerization of ethyl acrylate. Accordingly, the reaction mixture should be properly inhibited to reduce the polymerization of ethyl acrylate. There are many known inhibitors which can be used. Among those inhibitors commonly used to inhibit the polymerization of ethylenically saturated organic compounds include phenothiazine, methylene blue, hydroquinone, all of which can be used preferably in the presence of oxygen; and phenolic type inhibitors such as catechol, resorsinol, dihydroxyxylene, methoxy phenol such as guaiacol and p-methoxy phenol, pyrogallol, methyl pyrogallol, cresols, phenol, xylenols, and the like.

The molar ratios of ethanol to ethyl acrylate can vary within a relatively wide range such as from 0.5:1 to about 2:1. Greater amounts of ethanol have been found to result in the formation of unacceptable levels of the diethyl ether by-product. Accordingly, it is preferred to lower the amount of ethanol. Thus, preferred molar ratios of ethanol to ethyl acrylate range from 0.5:1 to about 1:1. Molar ratios of catalyst to ethyl acrylate can range from about 0.05:1 to about 0.5:1. Preferred molar ratios of catalyst to ethyl acrylate will be in the range of from about 0.1:1 to about 0.4:1.

While the above description and examples below are limited to the formation of EEP, the present invention has broader potential. For example, the present invention is also applicable to the acid catalyzed addition of $C_1$–$C_{10}$ alkyl alcohols to alkyl acrylate esters in which the ester group contains from 1–10 carbon atoms to form alkyl 3-alkoxy propanates in the same manner depicted in equation 1 above. It is believed that process conditions such as temperature and pressure should generally fall within the broad ranges previously disclosed. Obviously, increased pressure such as needed when ethanol is the reactant may not be needed for higher alcohols which have higher boiling points. In general, it is believed that the molar ratios of alcohol to alkyl acrylate should fall within the broad ranges described above.

In general, all reactions can be accomplished under batch or continuous processes. The above invention will now be illustrated by the following examples which are not to be construed so as to strictly limit the invention as hereinafter claimed to the embodiments shown therein.

EXAMPLES 1-14

A series of batch experiments was run in order to determine the effect several variables had on the formation of EEP using the acid catalyzed addition of ethanol to ethyl acrylate. In all the examples, methane sulfonic acid (MSA) was used as the catalyst. The molar ratio of MSA to ethyl acrylate in all cases was 0.2:1. Further, all of the reactions included inhibitors of phenothiazine in amounts of 400–1,000 ppm and air. Table 1 illustrates the time, temperature, and molar ratios of reactants utilized, as well as the relative amounts of product and by-product which were formed.

TABLE I $CH_3SO_3H$ Catalyzed Addition of Ethanol To Ethyl Acrylate at Various Conditions

| Example No. | Time hrs | Temp. °C. | EtOH:EtAcA mole ratio | Wt % EEP | Wt % Et20 | EEP:Et20 mole ratio |
|---|---|---|---|---|---|---|
| 1 | 4 | 80 | 2:1 | 1.0 | — | — |
| 2 | 24 | 80 | 2:1 | 13.4 | — | — |
| 3 | 30 | 80 | 2:1 | 17.4 | — | — |
| 4 | 3 | 100 | 2:1 | 11.1 | 0.74 | 7.6 |
| 5 | 6 | 110 | 2:1 | 31.0 | 4.2 | 3.7 |
| 6 | 2 | 125 | 2:1 | 34.1 | 11.4 | 1.5 |
| 7 | 4 | 125 | 2:1 | 38.7 | 17.2 | 1.1 |
| 8 | 6 | 125 | 2:1 | 40.9 | 21.3 | 0.97 |
| 9 | 2 | 150 | 2:1 | 29.0 | 24.6 | 0.60 |
| 10 | 2 | 200 | 2:1 | 11.2 | 35.5 | 0.16 |
| 11 | 4 | 110 | 1:1 | 17.5 | 0.8 | 11.1 |
| 12 | 4 | 125 | 1:1 | 35.4 | 2.7 | 6.7 |
| 13 | 4 | 140 | 1:1 | 47.2 | 7.2 | 3.3 |
| 14 | 4 | 133 | 0.5:1 | 27.2 | 0.8 | 17.2 |

Examples 1-3 were run by refluxing a solution of ethanol and ethyl acrylate at atmospheric pressure and about 80° C. The rate of EEP formation was quite low with the reaction mixture consisting only of 17% EEP even after 30 hours.

In order to operate at higher temperatures, a series of reactions (Examples 4–10) was run in sealed glass tubes at the various temperatures and reaction times shown in Table 1. It was found that at the higher temperatures the rate of EEP formation was accelerated. However, diethyl ether was also formed. As the temperature was increased to 150° C., the yield of EEP dropped and a further drop in EEP production was found at 200° C.

Examples 11-13 were an attempt to reduce the diethyl ether by-product formation. Thus, the mole ratio of ethanol to ethyl acrylate was reduced to 1:1. As can be seen from Table 1, by lowering the amount of ethanol reactant, the diethyl ether by-product was drastically reduced. Example 14 was run at an even lower level of ethanol. While the diethyl ether by-product was greatly reduced, the accountabilities of the ethyl acrylate were generally poor and were highly variable. It is believed that ethyl acrylate was being lost to oligomers and other side reactions.

EXAMPLES 15-17

In these examples, a series of runs was made in order to determine if the MSA catalyst could be recycled. In Example 15, the named reactants were reacted at 128°–130° C. for 4 hours in the presence of MSA and the product, ethyl 3-ethoxy propanoate, was recovered by distillation. The heavy ends (H.E.) were then added to a new charge of reactants in Example 16 and reacted in a similar manner. After distillation to remove product, the heavy ends (H.E.) were again used to manufacture the product in Example 17.

All reactions were run in a stirred autoclave and then analyzed. Vacuum distillation was used to remove reactants and products from each reaction. On the third recycle, more catalyst had to be added because the catalyst was consumed by conversion to the ethyl ester. In general, the ethyl acrylate and ethanol efficiencies to EEP were above 90% The accountabilities of ethyl acrylate were only about 90% and those of ethanol were lower at about 80-85%. It is uncertain why the ethanol accountabilities were lower than those of the ethyl acrylate. Table II illustrates the results of the recycle experiment.

TABLE II

MSA Catalyzed Addition of Ethanol To Ethyl Acrylate; Recycle of Catalyst

| Example No. | Cycle # | Temp. °C. | Time hr. | Charged | Amt. g | EtAcA[1] % EFF % Conv. | EEP[4] | Others | % Account | EtOH[5] % EFF % Conv. | EEP | Et2O[6] | % Account |
|---|---|---|---|---|---|---|---|---|---|---|---|---|---|
| 15 | 1 | 128–130 | 4 | MSA[3] | 11.9 | 39.3 | 94 | 6 | 83 | 45.9 | 89 | 11 | 75 |
|  |  |  |  | EtAcA | 53.8 |  |  |  |  |  |  |  |  |
|  |  |  |  | EtOH | 24.8 |  |  |  |  |  |  |  |  |
|  |  |  |  | PTZ[2] | 0.054 |  |  |  |  |  |  |  |  |
|  |  |  |  | Distilled at 5 mm Hg absolute; max. temp. 66° C. - recovered 12.3 g cat. H.E. |  |  |  |  |  |  |  |  |  |
| 16 | 2 | 128–132 | 4 | H.E.[7] | 12.3 | 36.8 | 95 | 5 | 92 | 42.3 | 89 | 11 | 84 |
|  |  |  |  | EtAcA | 53.4 |  |  |  |  |  |  |  |  |
|  |  |  |  | EtOH | 25.3 |  |  |  |  |  |  |  |  |
|  |  |  |  | PTZ | 0.054 |  |  |  |  |  |  |  |  |
|  |  |  |  | Distilled at 3 mm Hg absolute; max. temp. 90° C. - recovered 8.9 g cat. H.E. |  |  |  |  |  |  |  |  |  |
| 17 | 3 |  |  | H.E. | 8.9 | 38.6 | 87 | 13 | 92 | 41.3 | 87 | 13 | 83 |
|  |  |  |  | MSA | 4.0 |  |  |  |  |  |  |  |  |
|  |  |  |  | EtAcA | 53.6 |  |  |  |  |  |  |  |  |
|  |  |  |  | EtOH | 25.6 |  |  |  |  |  |  |  |  |
|  |  |  |  | PTZ | 0.05 |  |  |  |  |  |  |  |  |

[1] ethyl acrylate
[2] phenothiazine
[3] methane sulfonic acid
[4] ethyl 3-ethoxypropanoate
[5] ethanol
[6] diethyl ether
[7] heavy ends

What is claimed is:

1. A process for the preparation of ethyl 3-ethoxy propanoate comprising reacting ethanol and ethyl acrylate in a mol ratio of from about 0.5:1 to about 2:1 at a temperature of between 120°–150° C. in the presence of an acid catalyst of the group consisting of hydrochloric acid, sulfuric acid, phosphoric acid, methane sulfonic acid, benzene sulfonic acid, toluene sulfonic acid, and sulfonic acid-type ion exchange resins.

2. The process of claim 1 wherein the temperature of reaction is between about 120°–130° C.

3. The process of claim 1 wherein the molar ratio of ethanol to ethyl acrylate is from about 0.5:1 to about 1:1.

4. The process of claim 1 wherein the molar ratio of said acid catalyst to ethyl acrylate ranges from about 0.05:1 to about 0.5:1.

5. The process of claim 1 wherein said acid catalyst is methane sulfonic acid.

* * * * *